Figure 1:
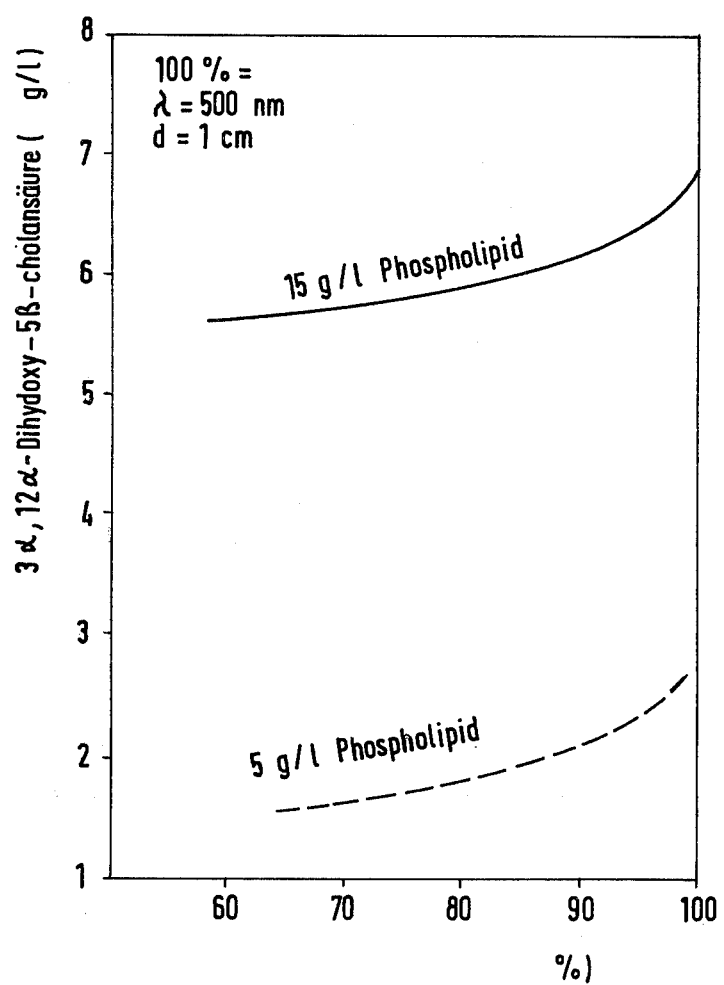

United States Patent [19]

Mader et al.

[11] 4,005,190

[45] Jan. 25, 1977

[54] INFUSION SOLUTION FOR PARENTERAL FEEDING

[75] Inventors: Helmut Mader, Furth; Werner Fekl, Erlangen; Klaus Schultis, Frankfurt, all of Germany

[73] Assignee: J. Pfrimmer & Co., Erlangen, Germany

[22] Filed: Apr. 2, 1975

[21] Appl. No.: 564,453

[30] Foreign Application Priority Data

July 10, 1974 Germany .......................... 2433173

[52] U.S. Cl. ............................... 424/127; 424/199; 424/201; 424/236; 424/237; 424/252; 424/255; 424/263; 424/280; 424/284; 424/319; 424/331; 424/334; 424/343; 424/357; 424/358; 424/365

[51] Int. Cl.$^2$ ....................................... A61K 33/00

[58] Field of Search .......... 424/236, 344, 357, 358, 424/127

[56] References Cited

UNITED STATES PATENTS

| | | | |
|---|---|---|---|
| 2,303,236 | 11/1942 | Shelton et al. | 424/357 |
| 2,972,565 | 2/1961 | Zilversmit | 424/358 |
| 3,169,094 | 2/1965 | Wretlind | 424/358 |
| 3,216,897 | 11/1965 | Krantz et al. | 424/358 |
| 3,708,583 | 1/1973 | Winstrom et al. | 424/344 |

OTHER PUBLICATIONS

Roessler, R. et al, Chemical Abstracts 76: 17803(f) (1972).
Merck Index 8th Edition (1968) pp. 181, 876–877.
Wilson et al, Textbook of Organic Medicinal and Pharm. Chem. (1962) pp. 635–637.

Primary Examiner—Norman A. Drezin
Attorney, Agent, or Firm—Burns, Doane, Swecker & Mathis

[57] ABSTRACT

An improvement in infusion solutions for parenteral solutions containing normally water-insoluble lipids and/or essential fatty components is disclosed. A minor amount sufficient to solubilize the said normally water-insoluble lipids and fatty components of a solubilizing mixture of ethanol and at least one member selected from the group consisting of propanediol, butane diol and hydroxy-substituted cholanic acid derivatives is mixed with the infusion solution to obtain a clear, pyrogen-free solution.

1 Claim, 2 Drawing Figures

INFUSION SOLUTION FOR PARENTERAL FEEDING

Parenteral feeding with solutions of amino acids and carbohydrates has been used for a long time. The addition of fats to such solutions for parenteral application is generally desirable but remains difficult since the fats must be emulsified in the solution. Various emulsifying agents for emulsifying fats in solutions for parenteral feeding are known in the art. For example, lectithin can be used an as emulsifier as described in German Pat. No. 1,049,540. According to the German published application 1,249,459, egg phosphatides are used also as emulsifiers for soybean oil. U.S. Pat. No. 2,727,706 discloses the use of gelatins or mono and diglycerides of fatty acids as emulsifiers for fatty acids in intravenous injection compositions. It is also known, for example, from German published application 1,792,294, that essential amino acids can be present in the infusion solution with the emulsified fat as well as glycerin and other higher polyalcohols, such as sorbitol or xylitol. According to the German published application 1,934,317, in the production of these infusion preparations, aqueous solutions of the soluble components are each separately sterilized, the fatty emulsion is separately sterilized, and thereafter the materials are then intermixed.

The use of parenteral infusion solutions containing such fatty emulsions can show, however, various acute and undesirable effects, such as, for example, thermogenic and pyrogenic reactions with nausea, vomiting, headaches and other such unpleasant effects. Also, colloidal reactions such as chest pains, cyanosis etc. are frequently observed. The stability of these preparations is relatively poor and agglomerations of the fat and oil particles of the dispersion or emulsion often occur during storage. Storage conditions must be limited in most cases to about 4° C. A perfect approval of the emulsions prior to their use is difficult or impossible because of the nontransparency of the infusion liquid.

The need for certain essential fatty acids in the feeding of the human being has been known for a long time. As early as 1929, Burr and Burr ("A New Deficiency Disease Produced by the Rigid Exclusion of Fat from the Diet", J. Biol. Chem. 82 (1929), 345), observed in an animal experiment in the case of a diet without fat, serious growth disturbances and other pathological changes especially in the hair and on the skin. The symptoms disappeared after administration of linoleic acid. Other complaints also have been traced back to the lack of essential fatty acids. In the case of patients with a posttraumatic and postoperative catabolism, a strong drop in essential fatty acids can be observed in the serum even within a few days, as can be gathered from the work of U. Troll and P. Rittmeyer in Infusion Therapy, No. 3, page 230 (1974). Therefore, it is necessary that in parenteral feeding that not only are the customary fats and oils supplied but also essential fatty acids.

The present invention provides a solution for total parenteral feeding which closes the present medication gap and which surprisingly fulfills all requirements of the parenteral feeding by containing all required substrata in a clear, sterile, pyrogen-free solution. The albumin requirement is provided by a suitable mixture of amino acids, the carbohydrate requirement preferably by polyols, such as xylitol, sorbitol or glycerin and the essential fatty acids requirement is preferably provided by phosphatides. Among others, choline esters of the diglyceride phosphoric acid (lecithin) are suitable phosphatides and particularly when the unsaturated fatty acid portion is relatively high. Other suitable lipids and essential fatty acid components known to the skilled artisan may also be utilized. Other carbohydrate metabolism substrata, such as for example ethanol, may be present. Other conventional, physiologically compatible ingredients may also be present.

According to the present invention, the parenteral infusion solution contains a minor amount sufficient to solubilize the water-insoluble lipids and fatty components of ethanol and at least one member selected from the group consisting of propanediol, butanediol and derivatives of hydroxy-substituted cholanic acid. Utilization of these materials as solvent intermediaries for the normally water-insoluble lipids and fatty components results in a clear, pyrogen-free aqueous solution. The quantity of ethanol generally should not exceed 50 g per liter, while the divalent alcohols, that is, propanediol and butanediol, can be present individually or together up to about 100 g per liter of infusion solution. The infusion solution of the present invention preferably contains ethanol and a hydroxy-substituted cholanic acid derivative since the latter also will solubilize free fatty acids, especially essential fatty acids, or esters (such as the mono-ester) or salts thereof as well as fat soluble vitamins, such as vitamins A, E, D and K. It has been found that these free fatty acids and fat soluble vitamins form corresponding water soluble molecule compounds with the hydroxy-substituted cholanic acid derivatives in the presence of the alcohol and thus can also become a component of the total parenteral nutritive solution. The preferred hydroxy-substituted cholanic acid derivatives for use in the present invention are $3\alpha$, $12\alpha$-dihydroxyl-$5\beta$-cholanic acid and $3\alpha$, $7\alpha$, $12\alpha$-trihydroxy-$5\beta$-cholanic acid or their salts, and mixtures thereof.

The hydroxy-substituted cholanic acid derivatives are present in the infusion solution in an amount sufficient to yield a weight ratio of normally water-insoluble phosphatides to hydroxy-substituted cholanic acid derivatives of from about 1:1 to 3:1. If the solution contains free fatty acids as water insoluble fatty components e.g. linoleic acid, a higher amount of hydroxy-substituted cholanic acid derivatives may be necessary to keep the solution clear.

The normally water-insoluble essential fatty acids-containing phosphatide, which can be present in a quantity up to 50 g/l, are kept in a clear solution by the use of the solubilizing mixture of the present invention of ethanol and at least one member selected from the group consisting of bivalent alcohols and hydroxy-substituted cholanic acid derivatives, so that with this for the first time an infusion solution is obtained which also contains the fat components in a clear solution and which therefore is particularly suited for the total parenteral feeding of patients.

Of particular importance is the fact that the hydroxy-substituted cholanic acid derivatives as well as the alcohol components used in the infusion solution of the present invention function not only as auxiliary solvent intermediary materials but also bring additional useful physiological effects to the infusion solutions and are incorporated in the metabolism of the organism. Surprisingly, the known hemolyzing effect of the $3\alpha$, $12\alpha$-dihydroxy-$5\beta$-cholanic acid and $3\alpha$, $7\alpha$, $12\alpha$-trihydroxy-5β-cholanic acid is completely neutralized in the infusion solution of the present invention in combination with other substrata, so that good physiological compatibility of the new infusion solution results.

Figure 2:
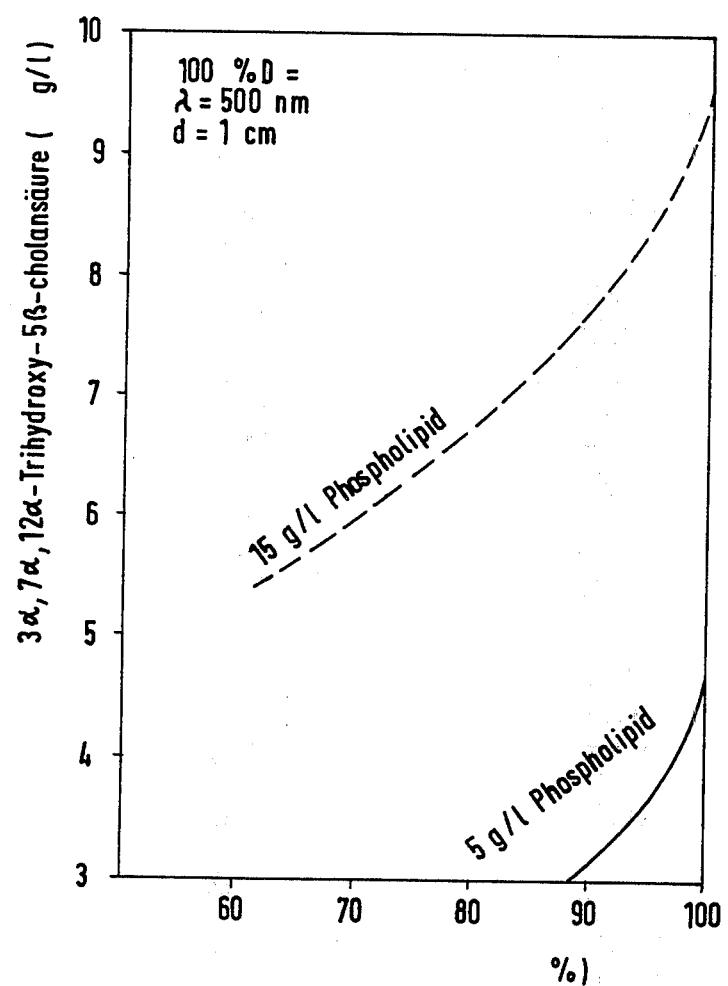

As noted above, the hydroxy-substituted cholanic acid derivatives are present in the infusion solution of the present invention in a weight ratio of the said normally insoluble phosphatides to the said acid derivatives of from about 1:1 to 3:1. The desired quantities of the preferred 3α, 12α-dihydroxy-5β-cholanic acid and 3α, 7α, 12α-trihydroxy-5β-cholanic acid compounds for a given solution can be easily determined by the skilled artisan. For example, FIGS. 1 and 2 illustrate the amounts necessary to obtain the desired permeability of a 100% clear solution containing 5 g/l and 15 g/l of phospholipids (phosphatides). These curves were obtained from the examples as set forth herein below. While it is apparent that the quantitative ratios of hydroxy-substituted cholanic acid derivatives and lipids are not linearly proportional, the curves exemplify the approximate relationship of lipids and hydroxy-substituted cholanic acid derivatives. The particular amount of hydroxy-substituted cholanic acid derivatives necessary for a particular quantity of water insoluble infusion components can be easily determined by the man skilled in the art.

The invention is additionally illustrated in connection with the following Examples which are to be considered as illustrative of the present invention. It should be understood, however, that the invention is not limited to the specific details of the Examples.

EXAMPLES

The following examples show the composition of infusion solutions of the present invention for total parenteral feeding of patients. The production of the infusion solution was accomplished in accordance with the present status of the art by stirring while slightly heating and with the use of a sequence of addition of the ingredients or a combination of groups of ingredients to the desired solution in a logical manner commensurate with the skill of the art. Additional quantities of the basic components, particularly sodium hydroxide can possibly be added for adjustment of the desired pH value.

The phospholipid used in the following examples was a purified phosphatiolefraction of the soya bean containing 95% phosphatidylcholine and ca. 5% phosphatidylethanolamine but also phospholipids of animal origin, e.g. egg lecithin, or other phospholipids can be used.

EXAMPLE I

An infusion solution was formed by the following components:

| | | |
|---|---|---|
| 1. | Sodium glycerophosphate . 5H$_2$O | 1.000 g |
| 2. | Sodium chloride | 1.227 g |
| 3. | Sodium acetate . 3H$_2$O | 1.905 g |
| 4. | Potassium chloride | 1.490 g |
| 5. | Potassium acetate | 0.489 g |
| 6. | Sodium hydroxide | 0.740 g |
| 7. | Potassium hydroxide | 0.561 g |
| 8. | Magnesium acetate . 4H$_2$O | 0.643 g |
| 9. | L-isoleucine | 0.780 g |
| 10. | L-leucine | 1.090 g |
| 11. | L-lysine HCl | 1.250 g |
| 12. | L-methionine | 1.050 g |
| 13. | L-phenylalanine | 1.090 g |
| 14. | L-threonine | 0.490 g |
| 15. | L-tryptophan | 0.220 g |

-continued

| | | |
|---|---|---|
| 16. | L-valine | 0.750 g |
| 17. | L-histidin | 0.490 g |
| 18. | L-arginine | 1.990 g |
| 19. | L-alanine | 3.000 g |
| 20. | L-prolin | 3.490 g |
| 21. | L-glutamic acid | 4.500 g |
| 22. | Glycocoll | 4.990 g |
| 23. | Sorbitol | 70.000 g |
| 24. | Xylitol | 40.000 g |
| 25. | Inositol | 0.200 g |
| 26. | Nicotinic acid amide | 0.020 g |
| 27. | Pyridoxine hydrochloride | 0.015 g |
| 28. | Riboflavin-5'-phosphoric acid ester, sodium salt | 0.002 g |
| 29. | Ethanol | 21.300 g |
| 30. | Phospholipid | 5.0 g |
| 31. | 3α, 7α, 12α-trihydroxy-5β-cholanic acid | 4.8 g |

The substances were combined with water for injection at 1000 ml, filled into infusion bottles at 250 ml and were sterilized. The solutions were used for continuous dripping over several weeks and showed good compatibility.

EXAMPLE II

An infusion solution was formed containing substances 1 – 30 as in Example I and also including

| | | |
|---|---|---|
| 31. | 3α, 12α-dihydroxy-5β-cholanic acid | 3.0 g |

The components were combined with water and sterilized in the same manner as Example I. Again, a compatible solution resulted.

EXAMPLE III

An infusion solution was formed containing substances 1 – 29 as in Example I and also including

| | | |
|---|---|---|
| 30. | Phospholipid | 15.0 g |
| 31. | 3α, 12α-dihydroxy-5β-cholanic acid | 7.0 g |

The compounds were combined with water and sterilized in the same manner as Example I. Again, a compatible solution resulted.

EXAMPLE IV

An infusion solution was formed containing substances 1 – 29 as in Example I and also including

| | | |
|---|---|---|
| 30. | linoleic acid | 3.0 g |
| 31. | 3α, 12α-dihydroxy-5β-cholanic acid | 12.0 g |

The compounds were combined with water and sterilized in the same manner as Example I. Again, a compatible solution resulted.

EXAMPLE V

An infusion solution was formed containing substances 1 – 31 as in Example II and also including

| | | |
|---|---|---|
| 32. | Vitamin A | 0.90 mg |
| 33. | Vitamin D$_2$ | 6.00 μg |
| 34. | Vitamin E | 10.00 mg |

| | | |
|---|---|---|
| 35. | Vitamin K$_1$ | 0.06 mg |

The compounds were combined with water and sterilized in the same manner as Example I. Again, a compatible solution resulted.

EXAMPLE VI

An infusion solution was formed containing substances 1 – 29 as in Example I and also including

| | | |
|---|---|---|
| 30. | Phospholipid | 3.0 g |
| 31. | Propanediol | 50.0 g |
| 32. | Butanediol | 50.0 g |

The components were combined with water and sterilized in the same manner as Example I. Again, a compatible solution resulted.

EXAMPLE VII

An infusion solution was formed containing substances 1 – 29 as in Example VI and also including

| | | |
|---|---|---|
| 30. | Phospholipid | 15.0 g |
| 31. | Butanediol | 80.0 g |
| 32. | 3α, 12α-dihydroxy-5β-cholanic acid | 6.0 g |

The components were combined with water and sterilized in the same manner as Example I. Again, a compatible solution resulted.

EXAMPLE VIII

An infusion solution was formed containing substances 1 – 28 as in Example I and also including

| | | |
|---|---|---|
| 29. | Ethanol | 50.0 g |
| 30. | Phospholipid | 50.0 g |
| 31. | 3α, 12α-dihydroxy-5β-cholanic acid | 19.0 g |

The components were combined with water and sterilized in the same manner as Example I. Again, a compatible solution resulted.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

We claim:

1. In an infusion solution for parenteral feeding which comprises water-soluble amino acids, polyols, minerals and vitamins and water-insoluble components comprising phosphatides or phosphatides and vitamins A, E, D and K, the improvement which comprises including in the infusion solution an amount sufficient to solubilize the water-insoluble components of a solubilizing mixture of ethanol and at least one member selected from the group consisting of 3α, 12α-dihydroxy-5β-cholanic acid and 3α, 7α, 12α-trihydroxy-5β-cholanic acid or their salts, the said cholanic acid compounds or their salts being present in the infusion solution in an amount sufficient to yield a weight ratio of water-insoluble phosphatides to cholanic acid compounds or their salts of from about 1:1 to 3:1, whereby the infusion solution is maintained in clear solution.

* * * * *